(12) United States Patent
Gracies et al.

(10) Patent No.: US 12,350,062 B2
(45) Date of Patent: Jul. 8, 2025

(54) ANALYSIS SYSTEM WITH A PORTABLE CONNECTED DEVICE

(71) Applicants: Université Paris—Est Créteil Val de Marne, Créteil (FR); Assistance Publique—Hôpitaux de Paris, Paris (FR)

(72) Inventors: Jean-Michel Gracies, Paris (FR); Samer Mohammed, Thiais (FR)

(73) Assignees: Université Paris—Est Créteil Val de Marne, Créteil (FR); Assistance Publique—Hôpitaux de Paris, Paris (FR)

( * ) Notice: Subject to any disclaimer, the term of this patent is extended or adjusted under 35 U.S.C. 154(b) by 772 days.

(21) Appl. No.: 17/552,894

(22) Filed: Dec. 16, 2021

(65) Prior Publication Data

US 2022/0192582 A1  Jun. 23, 2022

(30) Foreign Application Priority Data

Dec. 17, 2020 (EP) .................................... 20215114

(51) Int. Cl.
*A61B 5/00* (2006.01)
*A61B 5/11* (2006.01)

(52) U.S. Cl.
CPC .......... *A61B 5/4082* (2013.01); *A61B 5/0002* (2013.01); *A61B 5/1114* (2013.01); *A61B 5/702* (2013.01); *A61B 2562/0219* (2013.01)

(58) Field of Classification Search
CPC ..... A61B 5/683; A61B 5/6831; A61B 5/6824; A61B 5/6825; A61B 5/6826; A61B 5/6813; A61B 5/1124; A61B 5/1125; A61B 5/1112; A61B 5/1113; A61B 5/1114; A61B 5/11; A61B 5/1101; A61B 5/107;
(Continued)

(56) References Cited

U.S. PATENT DOCUMENTS 5,275,174 A * 1/1994 Cook ..................... A61B 5/389
600/595
8,187,209 B1 * 5/2012 Giuffrida ............ A61M 5/1723
600/595
(Continued)

*Primary Examiner* — Eric F Winakur
*Assistant Examiner* — Noah M Healy
(74) *Attorney, Agent, or Firm* — Sughrue Mion, PLLC

(57) ABSTRACT

A portable device (1) for quantifying movements of pronation and/or supination of a person, and intended to be used when the person has the elbow on a horizontal support, comprising: a solid armature (2) with: means for attaching (4), configured to secure one hand of the person in the device (1); a central pivot element (5) intended to be in contact with the horizontal support, during the angular oscillations of the hand, between two opposed identical "first block angles" relative to a vertical position called "neutral position", the "first block angles" defining a "small amplitude", first means for blocking (8) the movement of pronation and the movement of supination of the elbow, at the two "first block angles"; second means for blocking (9) the movement of pronation and the movement of supination, at two identical opposed "second block angles" relative to the neutral position, between the solid armature (2) relative to the horizontal support, the "second block angles" defining a "large amplitude" greater than the "small amplitude"; an IMU (3) able to measure movement data.

14 Claims, 11 Drawing Sheets

(58) Field of Classification Search
CPC ... A61B 5/1071; A61B 5/4076; A61B 5/4082; A61B 5/4094; A61B 5/702; A61B 2562/0219
See application file for complete search history.

(56) References Cited

U.S. PATENT DOCUMENTS

2006/0052726 A1\* 3/2006 Weisz ................. A61B 5/1121
    600/595
2022/0160290 A1\* 5/2022 Ejaz .................... A61B 5/1125

\* cited by examiner

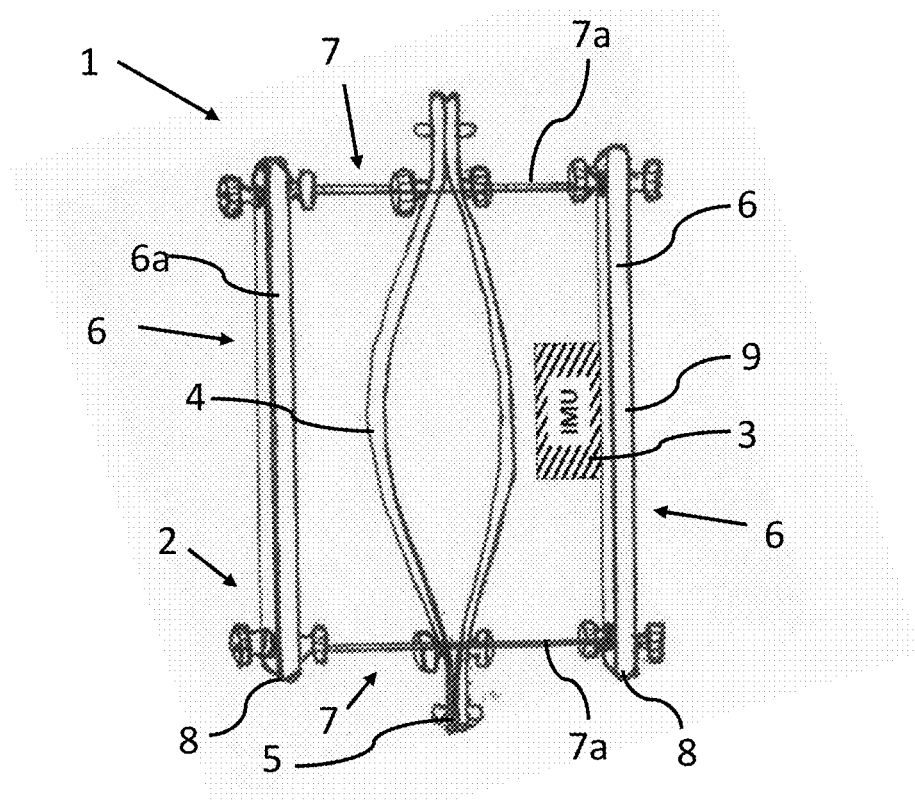
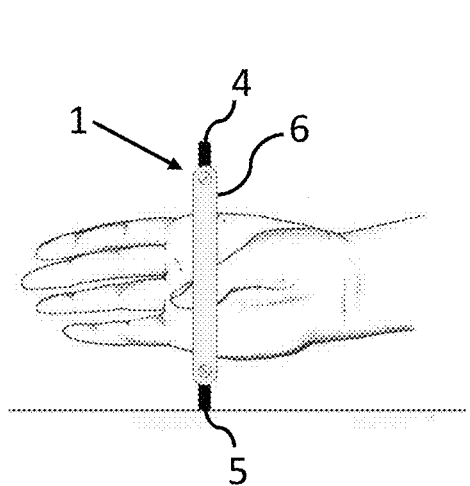 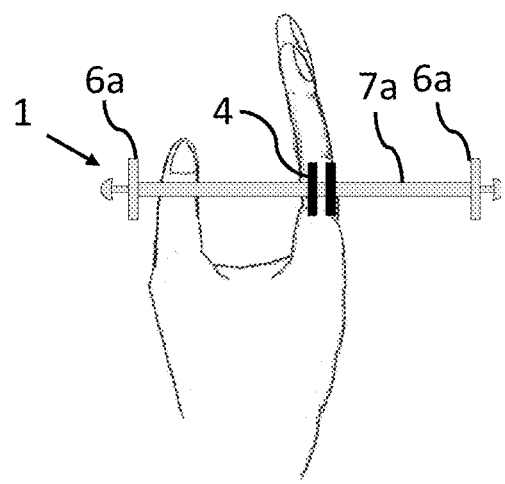
Figure 1
Figure 2  Figure 3

ANALYSIS SYSTEM WITH A PORTABLE CONNECTED DEVICE

FIELD OF THE INVENTION

The present invention relates to an analysis system for measuring movements of the elbow of a subject during pronation and/or supination.

STATE OF THE ART

The neurological disorders of movement, such as Parkinson's disease (PD), significantly impair Rapid Alternating Movements (RAM). Most everyday movements are rapid alternating movements (RAM). Parkinson's disease (PD) is an example of neurological disorders causing RAM impairment (dysdiadochokinesia).

However, other neurological or psychiatrical syndromes impair RAM, e.g. upper motor neuron dysfunction (stroke, multiple sclerosis, spinal cord or brain injury); cerebellar dysfunction (cerebellar lesion, essential tremor); sensory dysfunction (ataxia); other cortical dysfunction (atypical Parkinsonism, frontal disorders, apraxia); psychiatric conditions, such as depression, anxiety disorders, somatization disorders; orthopaedic limitations etc.

There is a variety of disease which impair hand movements, so that it is difficult for clinicians to make a diagnosis.

Consequently, tests of RAM are a standard and critical assessment in the clinical setting. Clinically, hypometric disorders (e.g. Parkinson's disease, spastic paresis) affect large movements more than small movements, whereas hypermetric disorders (e.g. cerebellar dysfunction, chorea) affect small movements more than large ones. In many situations, when diagnosing movement impairments, it is sometimes challenging for a clinician to distinguish a mild case of parkinsonian rest tremor from a mild case of cerebellar tremor.

In older studies, Wennberg, Beuter and their colleagues (Wennberg A, Hagman M, and Johansson L. *Preclinical neurophysiological signs of Parkinsonism in occupational manganese exposure. Neurotoxicology* 1992; 13(12), 271-274; Beuter A, Mergler D, Degeoffroy A, Carriere L, Belanger S, Varghese L, Sreekumar J, Gauthier S. *Diadochokinesimetry a study of patients with Parkinson's disease and manganese exposed workers. Neurotox* 1994; 15: 655-64) could demonstrate substantial quantitative differences in diadochokinesia (maximal movement amplitude, maximal movement frequency) between normal subjects and patients with PD, but also between normal subjects and subjects chronically exposed to manganese who had not been clinically diagnosed with parkinsonism. Thus, a method for quantifying diadochokinesia, usable in clinical practice, may provide a sensitive tool to detect conditions such as PD and chronic exposure to manganese early in the evolution, to help treat disorders before stages of disabling symptoms. The document US2006052726 (Donald Weisz, Jean Michel Gracies 2006) describes a device for the measurement of pronation and supination movements. This prior art device is suitable for measurement in the clinic and cannot perform the measurements remotely via a connection or perform the measurements outside the clinic. In addition, this prior art device does not give precise values of the patient's movements because the patient has to hold the device by exerting pressure with his/her fingers, which interferes with the results by the tonic contraction of the flexors of the fingers, necessary to hold the device, which in turn can tire after a few movements and disturb the performance of pronation and supination, leaving the results to the discretion of the clinician.

It is thus important for diagnostic and follow-up purposes to accurately establish the mechanism and monitor the severity of dysdiadochokinesia. Techniques measuring dysdiadochokinesia (dysdiadochokinesimetry) have been used in motor control laboratories with cumbersome machinery. However, using such equipment outside specific research studies is unrealistic in routine clinic practice. On the other hand, the tools currently used in clinical practice do not quantify RAM and measurement over two amplitudes of movement is currently not done at the clinic.

Studies and results on dysdiadochokinesia are often left to the subjective appreciation of the clinician (neurologist, rehabilitation physician or therapist).

To conclude, there is a need for objective quantification of rapid alternating movements over two different amplitudes, for example at the elbow for pronation and/or supination.

SUMMARY OF THE INVENTION

The present invention allows systematic quantification of movement frequency and acceleration profiles over at least two amplitudes and their comparison, as well as the acceleration peaks; the latter may be a powerful parameter to discriminate healthy from parkinsonian movements, based on our preliminary data. It may also help early diagnosis between mild forms of Parkinsonism and mild forms of cerebellar or executive disorders.

Here, the invention relates to a portable device for quantifying movements of pronation and/or supination of a person and intended to be used when the person has the elbow on a horizontal support.

The device comprises:
a solid armature with:
  means for attaching, configured to secure one hand of the person in the device, during the movements of pronation and/or supination;
  a central pivot element intended to be in contact with the horizontal support, during the angular oscillations of the hand, between two opposed identical "first block angles" relative to a vertical position called "neutral position", which are defined between the solid armature and the horizontal support,
  the "first block angles" defining a "small amplitude",
  first means for blocking the movement of pronation and the movement of supination of the elbow, at the two "first block angles";
  second means for blocking the movement of pronation and the movement of supination,
  at two identical opposed "second block angles" relative to the neutral position, between the solid armature relative to the horizontal support,
  the "second block angles" defining a "large amplitude" greater than the "small amplitude";
an IMU (Inertial Measurement Unit) able to measure movement data.

The present invention concerns also a system comprising:
portable device as defined previously,
means for filtering IMU data and calculating physical parameter related to movement data.
The physical parameter can be acceleration peak.
The means for calculating can be configured to calculate:
the maximal acceleration peak; and/or
the acceleration peak for each movement supination and/or pronation;

at least at the two "first block angles" and at the two "second block angles".

The present invention also concerns a method for quantification of rapid alternating movements over two different amplitudes, for pronation and/or supination of a subject, said method comprising:

measuring pronation and/or supination of a subject at two different amplitudes with at least one physical parameter;

comparing the physical parameter of said subject with the physical parameter of a reference over two different amplitudes; and detecting abnormal pronation and/or supination if value subject's physical parameter performance is different from physical parameter of said reference, for at least one amplitude.

The physical parameter can be acceleration peak. Advantageously taken at the "block angles".

Detection abnormal pronation and/or supination is made if value subject's physical parameter performance is different from physical parameter of said reference, for at least one amplitude of at least 20%, preferably at least 30%, more preferably at least 40%.

Thus, the present invention provides a portable, connected system called "portable connected alternometer" for easy and fast quantification of movements of pronation and/or supination of two pre-specified amplitudes, large (e.g. 180°) and small (e.g. 40°), thus particularly designed to diagnose and classify movement disorders such as parkinsonian or cerebellar disorders.

A standardized task can be performed by the user, comprising successive cycles of alternating forearm movements of pronation and/or supination of two different amplitudes. Multiple characteristics of the movement can be measured using one inertial measurement unit (IMU) to provide quantitative measurements of the user's motor skills, including peak acceleration and deceleration, movement frequency, mean excess or lack with respect to the requested movement amplitude, angular velocity, and normalized average rectified jerk measuring smoothness.

The device may guide the clinician in such circumstances, as parkinsonian disorders are characterized by hypo-acceleration ("lack of gas") while cerebellar disorders are characterized by hypo-deceleration (lack of brake). In addition, the device may help distinguish between PD patients on and off medication.

BRIEF DESCRIPTION OF THE DRAWINGS

Other advantages and characteristics of the disclosed devices and methods will become apparent from reading the description, illustrated by the following figures, where:

FIG. 1 represents a three-dimensional front view of the portable device;

FIG. 2 represents a three-dimensional side view of the portable device on a support and with a hand inserted in the device;

FIG. 3 represents a three-dimensional top view of the portable device with a hand inserted in the device;

GENERAL DESCRIPTION

Figure 4:
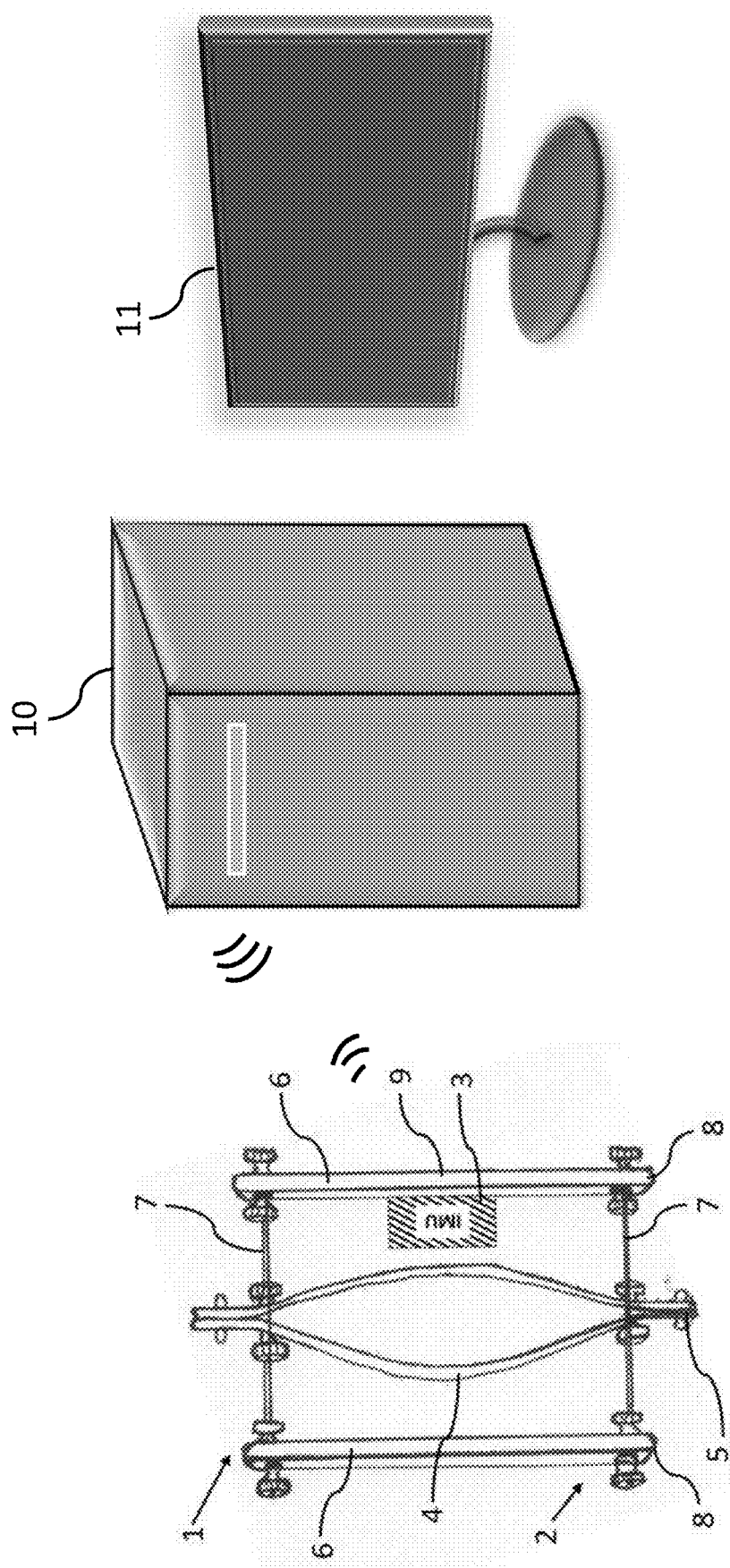
FIG. 4 represents a three-dimensional front view of the system comprising the portable device wirelessly connected to means for calculating and means for visualizing.
Figure 5:
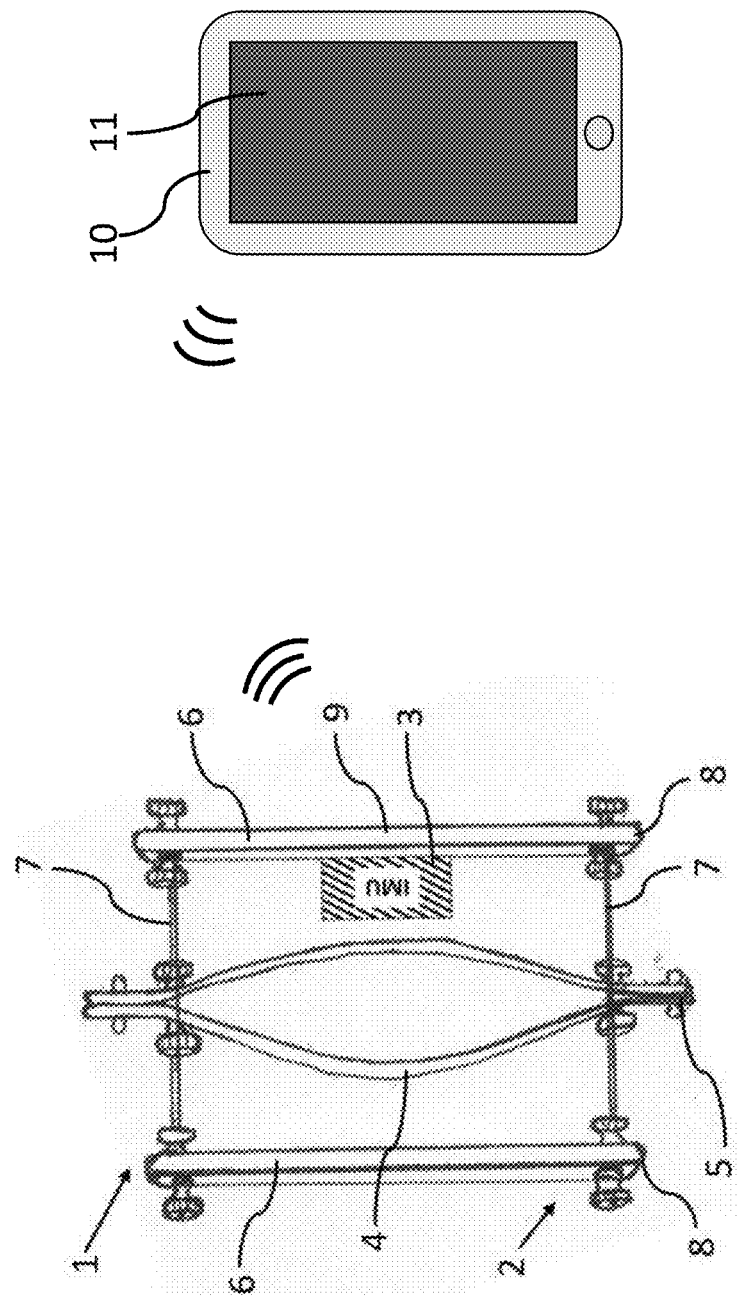
FIG. 5 represents a three-dimensional front view of the system comprising the portable device wirelessly connected to a phone which presents the means for calculating and the means for visualizing.
Figure 6:
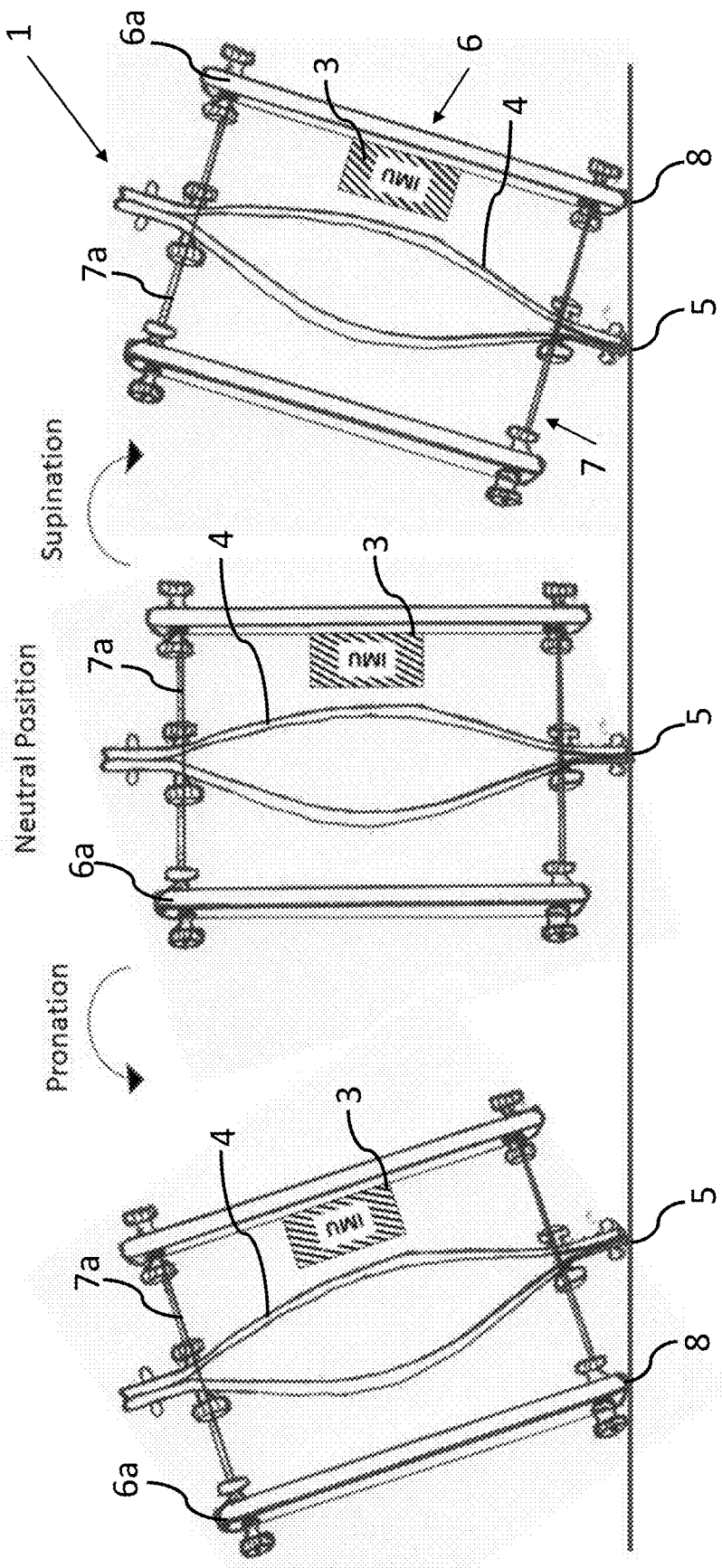
FIG. 6 represents a three-dimensional front view of the portable device during a pronation and supination movement over a small amplitude.
Figure 7:
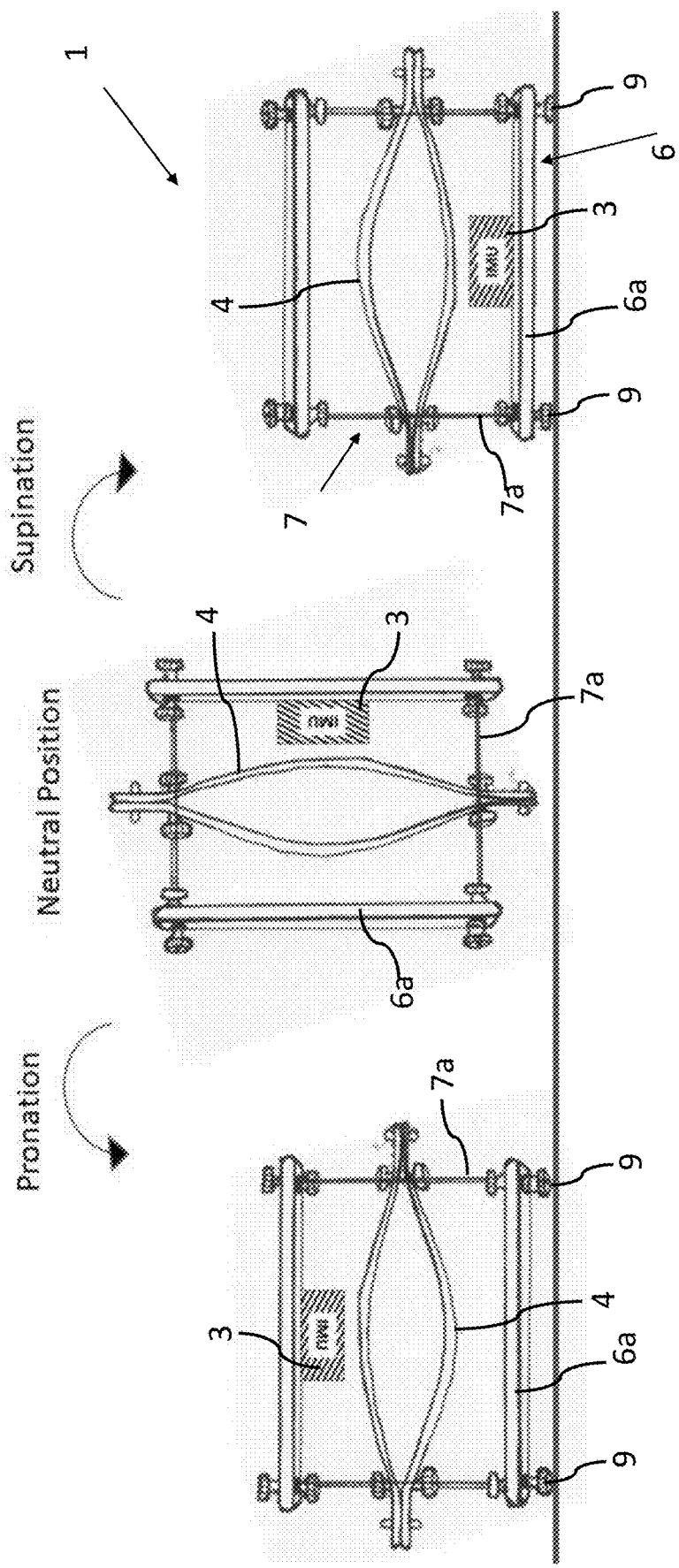
FIG. 7 represents a three-dimensional front view of the portable device during a pronation and supination movement over a large amplitude.

The invention relates to a system comprising a portable device 1 and some means for calculating 10 connected to the portable device 1. The portable device 1 is used for quantifying movements of pronation and/or supination of a person.

The system and the portable device 1 can be used to assist in decision making and diagnosis on patients.

Advantageously, the present invention makes it possible to evaluate whether the patient suffers from a motor problem such as Parkinson's disease.

The present invention may also help early diagnosis between mild forms of Parkinsonism and mild forms of cerebellar or executive disorders.

Most everyday movements are rapid alternating movements (RAM) and Parkinson's disease (PD) is the prototype of neurological disorders causing RAM impairment (dysdiadochokinesia). It is thus important for early diagnosis and follow-up purposes to accurately establish the mechanism and monitor the severity of dysdiadochokinesia.

Parkinson's disease is a disorder in which the initial bursts of movement acceleration are insufficient in size. Cerebellar disorders involve bursts of movement whose deceleration is insufficient.

The portable device 1 can measure the peak accelerations, decelerations, angle, speed, amplitude and smoothness in both directions of movements (pronation, supination) of at least two amplitudes.

A small amplitude movement to sensitize the examination toward disorders is characterized by insufficient deceleration, or inappropriate set shifting abilities, and a large amplitude movement to sensitize the examination towards disorders is characterized by insufficient acceleration.

Advantageously, the portable device 1 is intended to be used when the person has the elbow on a horizontal support.

Advantageously, the measurement over at least two amplitudes allows distinguishing between difficulties in scaling movements, from difficulties in alternating movement directions or deceleration impairments.

The system may guide the clinician in such circumstances, as parkinsonian (PD) disorders are characterized by hypo-acceleration ("lack of gas"), while cerebellar disorders are characterized by hypo-deceleration (lack of brake). In addition, the system may help distinguish between PD patients on and off medication.

The Portable Device 1

The portable device 1 allowing the dysdiadochokinesimetry (measurement of reciprocating movements) of elbow pronation and/or supination of at least two different amplitudes.

The device 1 is advantageously portable in the lab coat and quantifies the evaluation of maximal speed rapid alternating movements of at least two pre-specified amplitudes: small and large.

The movements involved with the portable device 1 are elbow pronation and/or supination of at least two distinct amplitudes.

The capacity to increase movement size (movement scaling) can be teased out from the capacity to alternate movement direction (set shifting), advantageously, by measuring the ratio of the large to the small movement frequency from the two tests (small and large amplitude movements).

The portable device 1 can allow the measure of the ratio of the maximal movement frequency over the large amplitude, to the maximal movement frequency over the small amplitude, which we call L/S ratio. Such measure may assist diagnosis, as large movements are more affected than small movements in motor disorders such as Parkinson's disease (PD), while it is the opposite in other diseases (e.g. frontal or cerebellar).

The device 1 is advantageously portable, connected, low-cost and measures movement over two amplitudes, a small and a large one.

The portable device 1 may also be used for rehabilitative purposes at home.

Advantageously, the portable device 1 may then provide feedback to the patient to train acceleration control, in disorders such as Parkinsonism, executive or cerebellar disorders.

Advantageously, the portable device 1 is configured to be used when the person has the elbow on a horizontal support.

The portable device 1 can comprise a solid armature 2 and an IMU 3 (inertial measurement unit).

The Solid Armature 2

1) Structure

The solid armature 2 can consist of a frame, with two parallel principal parts 6 with rigid bars 6a and nuts or screw associated for each one, mounted perpendicularly to two parallel transversal parts 7 with rigid rod 7a for each one.

The solid armature 2 has means for attaching 4, configured to secure one hand of the person in the device 1, during the supination and/or pronation movement and to apply pressure (a grip) around the person's hand so that the person's hand remains open and the device remains hooked to the hand.

The two rigid bars 6a can be firmly connected to the two parallel transversal rods 7a. Advantageously, the means for attaching 4 are mounted on the parallel transversal rods 7a, between the two parallel bars 6a.

The solid armature 2 has a central pivot element 5, intended to be in contact with the horizontal support, by its tip, during the angular oscillation of the hand that extends between two opposed "first block angles" relative to a neutral position. These angles are defined between the two parts of the solid armature 2 and the horizontal support.

Advantageously, the central pivot element 5 configured for resting in contact with the horizontal support, is the tip of the means for attaching 4. The "first block angles" define a "small amplitude", the neutral position is a vertical axis, and the hand of the person rests by its edge on the horizontal support.

The solid armature 2 has first means for blocking 8, configured to block the movements of pronation and/or the movements of supination of the elbow, at the two "first block angles".

Advantageously, the first means for blocking 8 are the tips of each rigid bar 6a, configured to be in contact with the table at the two opposed "first block angles". The rigid bars 6a are shorter than the tip 5 of the means for attaching 4, so that when the hand is inserted into the means for attaching 4, held in a vertical plane and resting on the table, the device 2 rests on the central pivot element 5 and can oscillate between supination and/or pronation under the action of the person's hand and forearm.

In other variants, the first means for blocking 8 can also be the screws or nuts that hold together each rigid parts 6a at its extremities with each transversal rod 7a. The first means for blocking 8 can also be the tips of the parallel rod 7a located in the bottom part of the solid armature 2.

The solid armature 2 has second means for blocking 9.

The second means 9 block the movements of pronation and/or the movement of supination, at two "second block angles" relative to the neutral position, between the solid armature 2 relative to the horizontal support.

Advantageously, the "second block angles" define a "large amplitude" greater than the "small amplitude".

The second means for blocking 9 are advantageously the principal parts 6 of the armature.

They can be the external plane surface of each rigid bar 6a.

In other variants, the second means for blocking 9 can be the screws or nuts that hold the solid armature 2 together.

Maximal pronation and supination in the "small amplitude" can be obtained by the contact between the tip of each rigid bar 6a and the table.

Advantageously, the maximal pronation and supination are comprised between 5° and 45° for the small movements Advantageously, the small amplitude can be defined by pronation of an angle of at least 13° from the neutral position, and by supination of an angle of at least 13° from the neutral position.

Full pronation and full supination of the forearm in the "large amplitude" can be obtained by turning the hand so that the palmar and dorsal rigid bars 6a are alternately placed flat on the table.

Advantageously, the large amplitude is defined by a pronation of 90° from the neutral position, and by a supination of 90° from the neutral position.

2) Details of Design

The means for attaching 4 can be two flexible strips fixated to the rods 7a, in their middle.

The means for attaching 4 can be a mounting system.

These flexible strips present extremities fixated by screws, nuts or other means, one end of which will be in contact with the horizontal support to be the central pivot element 5.

Advantageously, the flexible strips are used to firmly hold the hand of the subject during movements.

The flexible strips can be a low-density polyethylene (LDPE).

Advantageously, the flexible strips are configured to host the hand, and to be secured around the hand with their flexibility, so that the device remains stable and fixed on the hand, despite fast rotating and tapping movements of the hand.

The means for attaching 4 can be two flexible strips separated by a few centimeters and configured to allow the patient's hand to pass between the two flexible strips, the flexible strips spread apart and exert an important pressure on the patient's fingers or hand or elbow, allowing the device 1 to be held firmly without dropping, the device 1 remains hooked even when the patient makes movements.

In another embodiment, the means for attaching 4 or the flexible strips have a changeable length (with housing for instance) to modify the "first block angles" to be reached for the "small amplitude".

The parallel rods 7a can be horizontal threaded rods.

The parallel rods 7a can be situated at top and bottom of the solid armature 2 for securing the rigid bars 6a and the means for attaching 4.

Advantageously, the solid armature 2 consists of two rigid bars 6a mounted on the hand, parallel to the ulnar-radial styloid line.

The distance between the two rigid bars 6a can be adjustable (for instance may be modified along the parallel rods 7a which are threaded).

Advantageously, the means for blocking (first 8 and second 9) are changeable (adjustable) in their length.

Advantageously, the distance between the two rigid bars 6a is modified by the parallel rods 7a which are threaded.

The IMU 3

The IMU 3 can detect the acceleration and/or speed, and/or angular orientation, and/or frequency of the device 1, during the angular oscillations of the hand.

Advantageously, the IMU 3 is configured to measure the acceleration and/or speed, and/or angular orientation, and/or frequency of the device 1, at least at the two "first block angles" and at the two "second block angles".

The IMU 3 can be mounted on the solid armature 2.

Advantageously, the IMU 3 is mounted on one of the rigid bars 6a.

The IMU 3 can communicate wirelessly with a host computer or a smartphone.

Advantageously, the connection using WI-FI or Bluetooth between the IMU 3 that is mounted on the portable device 1 and the means for calculating 10 allows objective quantification of parameters that were not measurable with prior devices, particular peak accelerations and smoothness in both directions of the alternating movement.

In another embodiment, the IMU 3 is connected to means for storage.

The IMU presents means for storage data collected by the IMU 3.

Potentially, the portable device 1 can be used as a biofeedback rehabilitation system.

The device 1 can be used at home since the patient can practice his/her movements and be provided online with acceleration data.

In another embodiment, the IMU 3 can also be connected with the cloud so that measurements in real life can be performed and remotely communicated with therapists or physicians of the patient.

The data may also be securely stored off-line for later analysis by the physician.

The Means for Calculating 10

The system can quantify smoothness of the movement by calculating the patient's impulses, as well as amplitudes of motion and excess amplitudes of motion.

The system offers means for calculating 10, which can return graphs of patient results, and which are connected to the portable device. The results may assist in the diagnosis and/or be compared with the abilities of a healthy person to establish the patient's illness.

Figure 8:
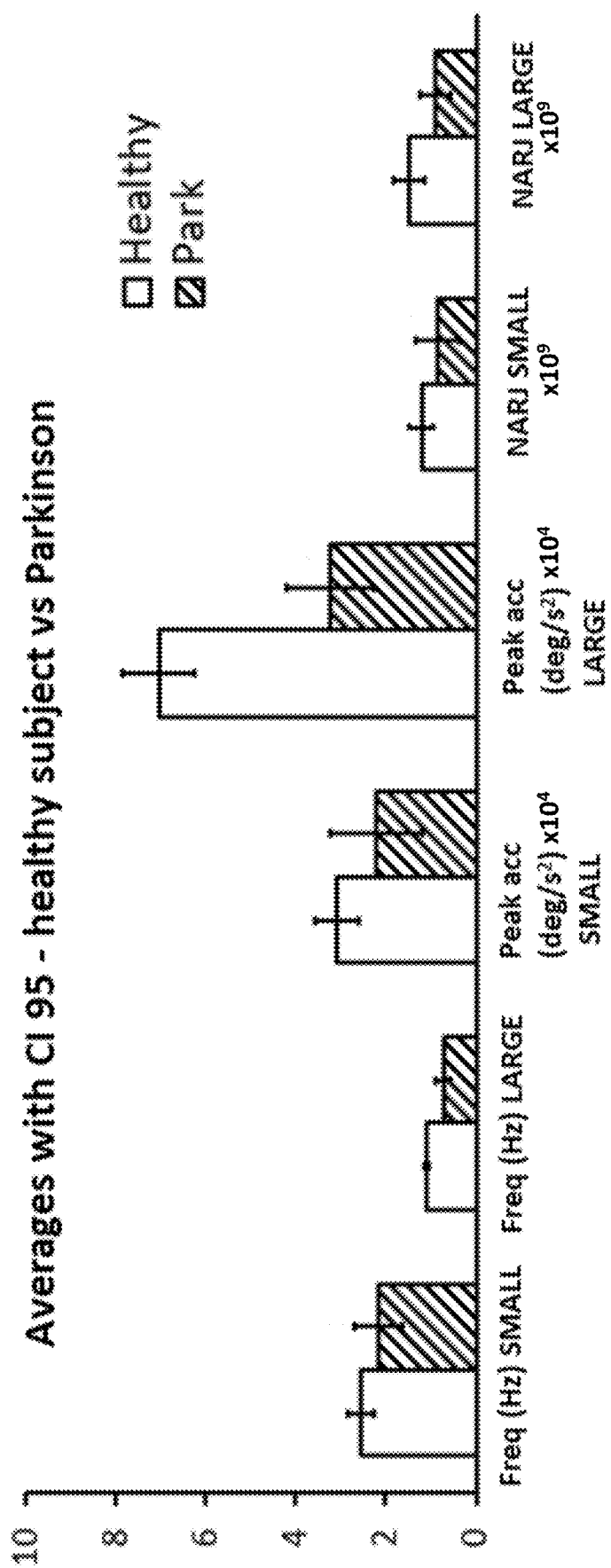
FIG. 8 represents a graph with mean data from healthy subjects compared to mean data from subjects with Parkinson's disease.
Figure 9:
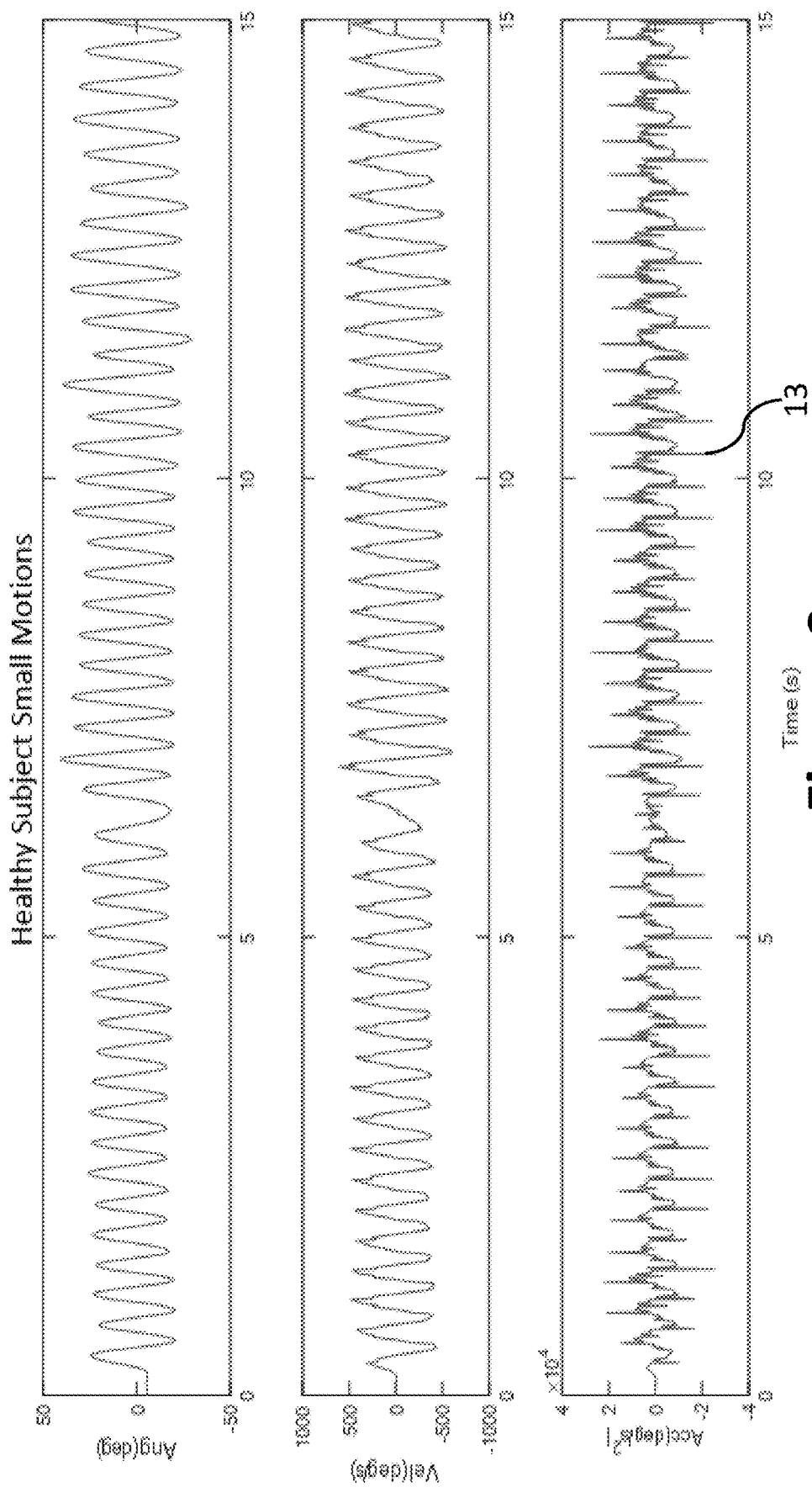
FIG. 9 represents graphs of the angle, speed and acceleration of a healthy patient during pronation and supination movements over a small amplitude.
Figure 10:
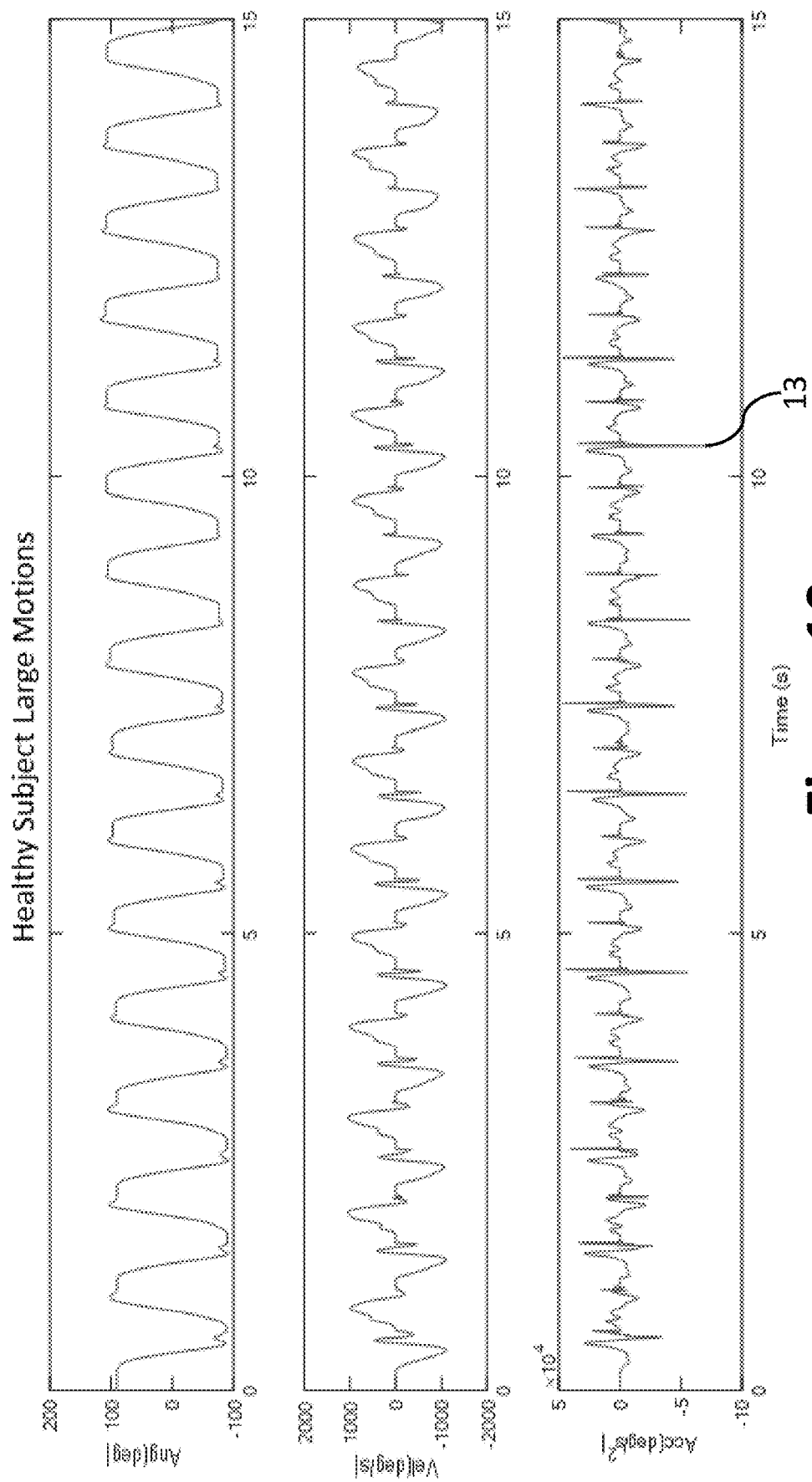
FIG. 10 represents graphs of the angle, speed and acceleration of a healthy patient during pronation and supination movements over a large amplitude.
Figure 11:
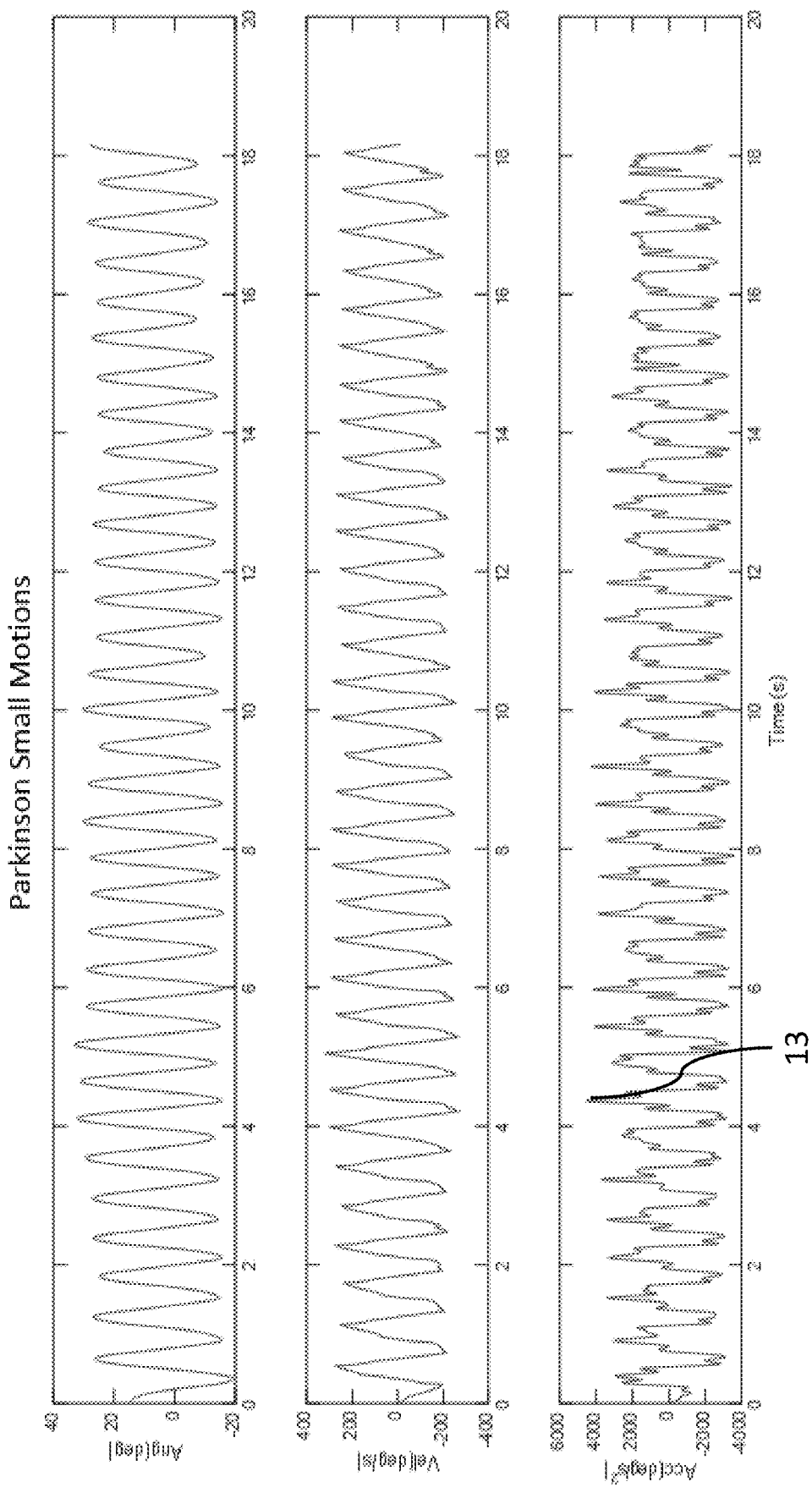
FIG. 11 represents graphs of the angle, speed and acceleration of a Parkinson patient during pronation and supination movements over a small amplitude.
Figure 12:
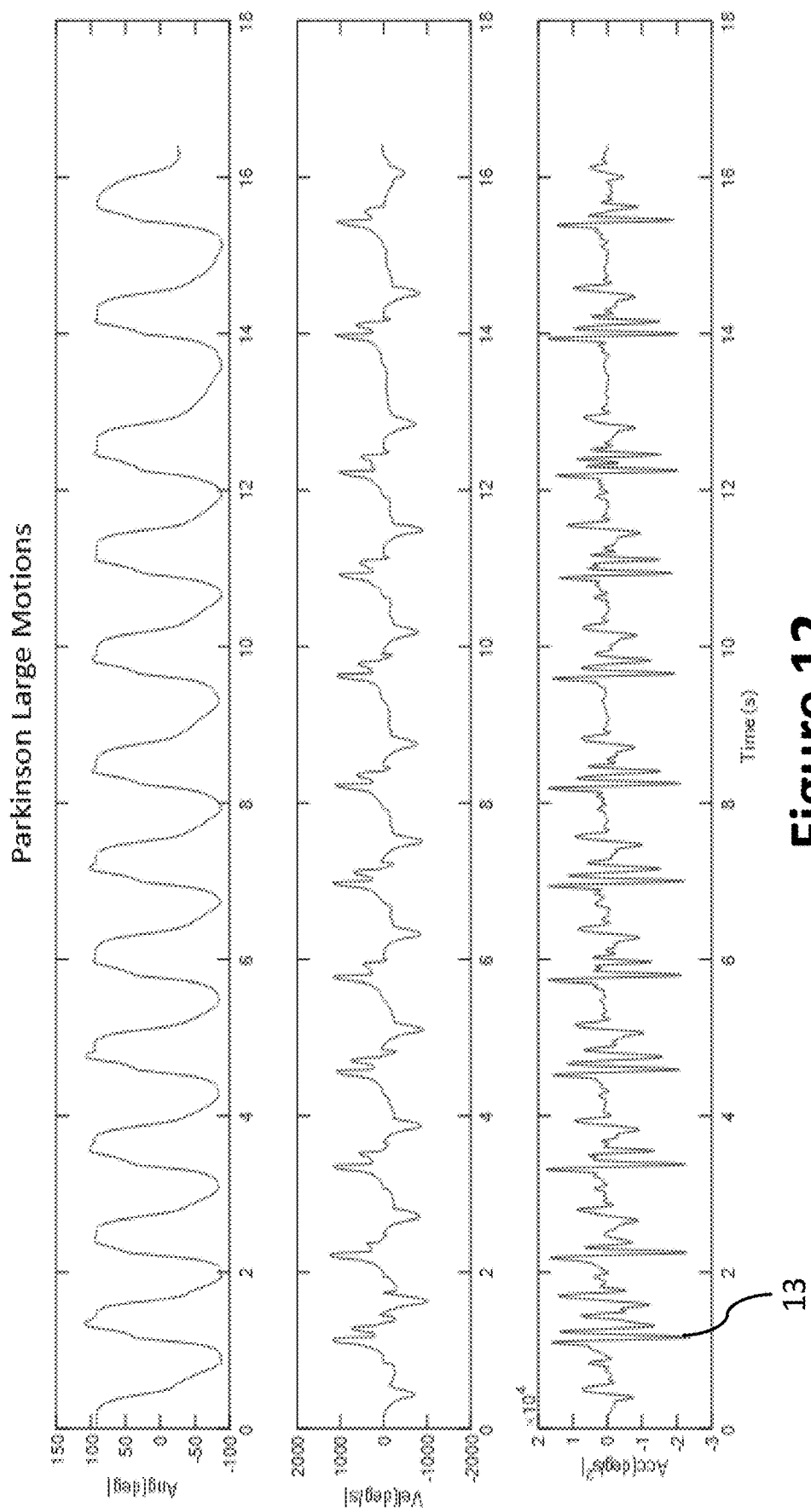
FIG. 12 represents graphs of the angle, speed and acceleration of a Parkinson patient during pronation and supination movements over a large amplitude.
Figure 13:
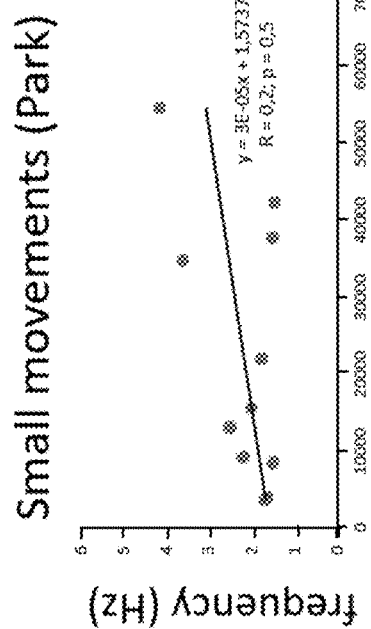
FIG. 13 represents a graph of the average frequency relative to the peak of maximum acceleration during several repetitions of a supination and pronation for small movements of a healthy subject.
Figure 14:
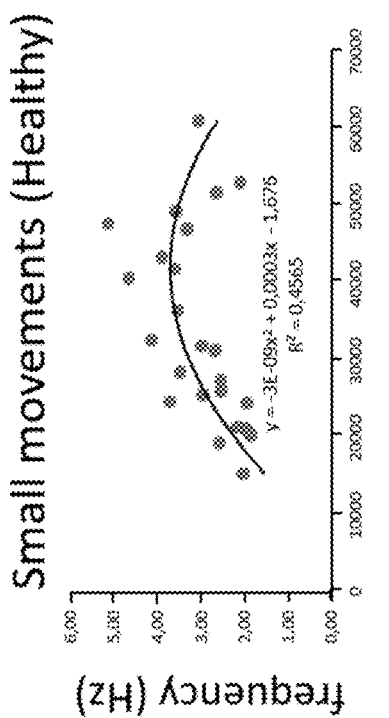
FIG. 14 represents a graph of the average frequency relative to the peak of maximum acceleration during several repetitions of a supination and pronation for large movements of a Parkinson subject.
Figure 15:
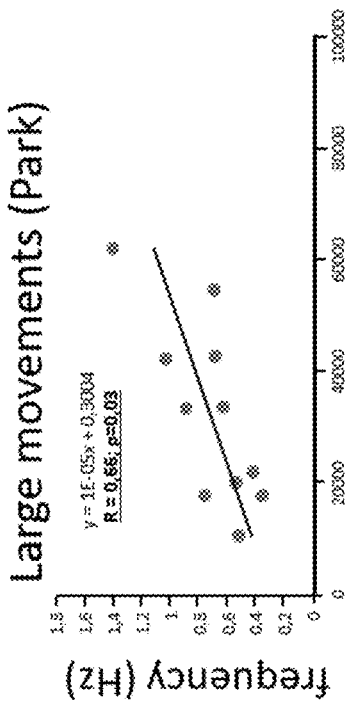
FIG. 15 represents a graph of the average frequency relative to the peak of maximum acceleration during several repetitions of a supination and pronation for small movements of a healthy subject.
Figure 16:
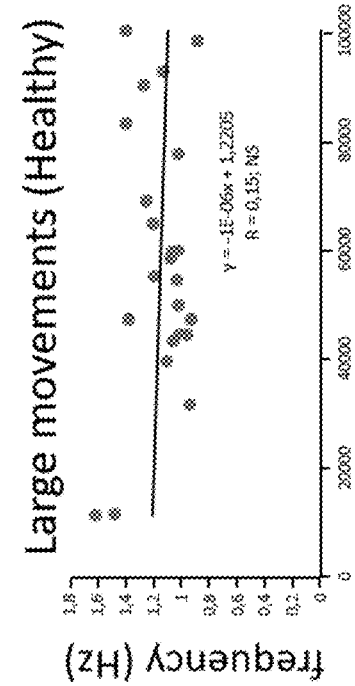
FIG. 16 represents a graph of the average frequency relative to the peak of maximum acceleration during several repetitions of a supination and pronation for large movements of a Parkinson subject.

For instance, a pre-study was conducted with the device 1 on 24 healthy subjects and 11 subjects with Parkinson's disease. The pre-study focused on the comparison between the two groups on two amplitudes (small and large) and by studying the movement frequency, acceleration peaks, and the NARJ (normalized average rectified jerk). The FIG. 8 provides data with 95% confidence intervals.

The frequency is determined by the number of complete movements (supination+pronation) per second.

The average frequency of healthy subjects over the small amplitude is 2.57 Hz while the average frequency of subjects with Parkinson's is 2.19 Hz, so there is a loss of around 0.4 Hz (16%) between the two groups.

The average frequency of healthy subjects over the large amplitude is 1.10 Hz while the average frequency of persons with Parkinson is 0.73 Hz, so there is a loss of around 0.4 Hz (36%) between the two groups.

In this particular sample of subjects, the absolute difference between the two groups is the same for both amplitudes but the relative difference for large movements is more than twice that for small movements, which identifies a specific pattern of movement difficulties that predominates on large movements and is consistent with the second sample of subjects presenting with Parkinson's disease.

The pre-study does an average of the maximal acceleration peak 13 for each patient in a group,
for a small amplitude: healthy subjects have an average of 31000 deg/s$^2$ while subjects with Parkinson's disease have an average of 21500 deg/s$^2$ (69% from normal);
for a large amplitude: healthy subjects have an average of 70500 deg/s$^2$ while subjects with Parkinson's disease have an average of 32500 deg/s$^2$ (46% from normal).

In both cases, the difference is marked, but this is particularly the case for large movements. This points to a diagnosis of hypometria, typical of Parkinson's disease, to be confirmed with the medical profile and clinical presentation of the patient.

The pattern typical of a subject with Parkinson's disease is marked by a reduction of the acceleration over both amplitudes but much more importantly during large amplitude movements.

The average acceleration peaks of a healthy person are higher than the average for a person with Parkinson's disease.

For instance, the graphs of a person with Parkinson's, will show acceleration peaks that are not constant during large amplitude exercise, hypothetically due to additional uncontrolled movements.

The means for calculating 10 can quantify the maximal acceleration 13 during the pronation and/or supination of the elbow.

Advantageously, the means for calculating 10 can be configured to calculate the ratio of the maximal movement frequency over the large amplitude to the maximal movement frequency over the small amplitude.

The ratio can determine the amplitude with the lowest frequency and be used for diagnostic purposes.

The means for calculating 10 can be configured to calculate the maximal acceleration peak 13; and/or the acceleration peak for each movement supination and/or pronation; at least over the two amplitudes.

The means for calculating 10 can be configured to calculate the smoothness of movement (for instance, using a normalized averaged rectified jerk—NARJ—which is an acceleration derivative).

The means for calculating 10 can be a computer, a laptop, a smartphone, or other device that can perform calculations.

Advantageously, the means for calculating 10 is connected wirelessly to the portable device.

In another embodiment, the system can comprise means for visualizing 11.

The Means for Visualizing 11

The means for visualizing 11 can be a screen linked or connected to the means for computing.

The means for visualizing 11 can be configured for showing the results.

Advantageously, the means for visualizing 11 can show the acceleration of the portable device.

The means for visualizing 11 can also show the movement amplitudes and speeds of pronation and/or supination.

The means for visualizing 11 can show a 3D representation of the person's movement.

Advantageously, the means for visualizing 11 indicate the angles to be reached with the portable device for the person.

The means for visualizing 11 can be a tablet, a smartphone or a computer.

The invention claimed is:

1. A portable device for quantifying movements of pronation and/or supination of a person, and intended to be used when the person has an elbow on a horizontal support, the portable device comprising:
    a solid armature comprising:
        means for attaching, configured to secure one hand of the person in the device, during the movements of pronation and/or supination;
        a central pivot element intended to be in contact with the horizontal support, during angular oscillations of the hand,
    between two opposed identical first block angles relative to a vertical position called neutral position, the first block angles being defined between the solid armature and the horizontal support and
    the first block angles defining a small amplitude,
        first means for blocking the movement of pronation and the movement of supination of the elbow, at the two first block angles; and
        second means for blocking the movement of pronation and the movement of supination,
    at two identical opposed second block angles relative to the neutral position, between the solid armature relative to the horizontal support,
    the second block angles defining a large amplitude greater than the small amplitude; and
    an Inertial Measurement Unit (IMU) configured to measure movement data, wherein the solid armature consists of a frame with: two parallel principal parts with rigid bars mounted perpendicularly to two parallel transversal parts with transversal rods, the means for attaching being mounted on the parallel transversal rods.

2. The portable device of claim 1, wherein the IMU is configured to measure: the acceleration and/or speed, and/or angular orientation, and/or frequency of the device, at least at the two first block angles and at the two second block angles.

3. The portable device of claim 1, wherein the first means for blocking are a tip of each rigid bar or a tip of one of the transversal rods, intended to be in contact with the horizontal support at the two opposed first block angles.

4. The portable device of claim 1, wherein the second means for blocking are the parallel principal parts.

5. The portable device of claim 1, wherein the means for attaching are longer than the rigid bars and their extremities is are the central pivot element.

6. The portable device of claim 1, wherein the distance between the two rigid bars is adjustable.

7. The portable device of claim 1, wherein the means for attaching are flexible strips.

8. The portable device of claim 7, wherein the flexible strips have a changeable length to modify the "first block angles".

9. The portable device of claim 1, wherein:
    the small amplitude is characterized by pronation of an angle of at least 13° from the neutral position, and by supination of an angle of at least 13° from the neutral position; and/or
    the large amplitude is characterized by a pronation of 90° from the neutral position, and by a supination of 90° from the neutral position.

10. A system comprising:
    portable device according to claim 1, and
    a computer device configured to communicate with the IMU, and calculate physical parameters related to the movement data measured by the IMU.

11. The system of claim 10, wherein the physical parameters include acceleration peak.

12. The system of claim 10, wherein the computer device is further configured to calculate:
    the maximal acceleration peak; and/or
    the acceleration peak for each movement of supination and/or pronation;
    at least at the two first block angles and at the two second block angles.

13. The system of claim 10, wherein the computer device is portable, and/or the portable device is connected wirelessly to the computer device.

14. The system of claim 10, wherein the physical parameters include peak acceleration and deceleration, movement frequency, mean excess or lack with respect to a requested movement amplitude, angular velocity, and normalized average rectified jerk measuring smoothness.

* * * * *